United States Patent
Nakao et al.

(10) Patent No.: US 6,706,939 B2
(45) Date of Patent: Mar. 16, 2004

(54) METHOD FOR CONCENTRATING 2,6-DIMETHYLNAPHTHALENE

(75) Inventors: Noboru Nakao, Kobe (JP); Koji Yamamoto, Kobe (JP); Masahiro Motoyuki, Kobe (JP)

(73) Assignee: Kobe Steel Ltd., Kobe (JP)

( * ) Notice: Subject to any disclaimer, the term of this patent is extended or adjusted under 35 U.S.C. 154(b) by 26 days.

(21) Appl. No.: 10/193,228

(22) Filed: Jul. 12, 2002

(65) Prior Publication Data

US 2003/0028064 A1 Feb. 6, 2003

(30) Foreign Application Priority Data

Jul. 13, 2001 (JP) .................................... 2001-214141

(51) Int. Cl.[7] ................................................. C07C 7/12
(52) U.S. Cl. .................... 585/820; 585/827; 585/828
(58) Field of Search ................ 585/820, 827, 585/828

(56) References Cited

U.S. PATENT DOCUMENTS

| | | | |
|---|---|---|---|
| 3,668,267 A | 6/1972 | Hedge | 585/831 |
| 4,791,235 A | 12/1988 | Maki et al. | 585/806 |
| 5,723,711 A | 3/1998 | Motoyuki et al. | 585/481 |
| 5,744,670 A | 4/1998 | Motoyuki et al. | 585/320 |
| 5,844,064 A | 12/1998 | Motoyuki et al. | 585/271 |
| 6,011,190 A | 1/2000 | Motoyuki et al. | 585/323 |
| 6,018,086 A | 1/2000 | Motoyuki et al. | 585/323 |
| 6,018,087 A | 1/2000 | Motoyuki et al. | 585/481 |
| 6,121,501 A | 9/2000 | Motoyuki et al. | 585/323 |
| 6,153,808 A | 11/2000 | Motoyuki et al. | 585/821 |
| 6,525,235 B2 | 2/2003 | Yoshida et al. | 585/814 |

FOREIGN PATENT DOCUMENTS

JP          6-65114          3/1994

OTHER PUBLICATIONS

A.V. Kiselev, et al., Adsorptionschromatographie, pp. 306–323, XP–002220765, "Gas–Und Flüssigkeits–Adsorptions–Chromatographie", 1985 (with English translation).
U.S. patent application Ser. No. 10/053,690, Motoyuki et al., filed Jan. 24, 2002.
U.S. patent application Ser. No. 10/076,431, Motoyuki et al., filed Feb. 19, 2002.
U.S. patent application Ser. No. 10/069,502, Yamamoto et al., filed Feb. 27, 2002.
U.S. patent application Ser. No. 10/193,228, Motoyuki et al., filed Jul. 12, 2002.

Primary Examiner—Walter D. Griffin
Assistant Examiner—Tam Nguyen
(74) Attorney, Agent, or Firm—Oblon, Spivak, McClelland, Maier & Neustadt, P.C.

(57) ABSTRACT

A method for concentrating 2,6-dimethylnaphthalene in a dimethylnaphthalene isomer mixture includes supplying the dimethylnaphthalene isomer mixture to an adsorption column packed with Y-type zeolite. In this instance, by setting the value derived from the expression $(u^{1/3}/\epsilon)d^{-5/3}$ at 14 $(m^{5/3} \ s^{-1/3} \ kg^{-1})$ or more, the concentration ratio of 2,6-dimethylnaphthalene to 2,7-dimethylnaphthalene can be 2.0 or more. u here represents the linear velocity (m/s) of the dimethylnaphthalene isomer mixture supplied to an adsorption column, $\epsilon$ represents the packing density $(kg/m^3)$ of Y-type zeolite, and d represents the grain size (m) of the Y-type zeolite.

5 Claims, 1 Drawing Sheet

US 6,706,939 B2

METHOD FOR CONCENTRATING 2,6-DIMETHYLNAPHTHALENE

BACKGROUND OF THE INVENTION

1. Field of the Invention

The present invention relates to methods for selectively concentrating 2,6-dimethylnaphthalene by adsorption in a mixture containing dimethylnaphthalene isomers.

2. Description of the Related Art

Polyethylene naphthalate (PEN) resins have excellent characteristics, including thermal resistance and impermeability to gases, which are not exhibited by well-known PET resins, and 2,6-dimethylnaphthalene (2,6-DMN) is a starting material for these polyethylene naphthalate resins.

Dimethylnaphthalene includes nine isomers. If 2,6-dimethylnaphthalene used for PEN contains the other isomers, the physical properties of the end product, that is, PEN, including thermal resistance and strength are degraded. Therefore, 2,6-dimethylnaphthalene must be separated out from the isomer mixture with high purity.

In particular, the physical properties of 2,6-dimethylnaphthalene are very close to those of 2,7-dimethylnaphthalene and, therefore, it is difficult to separate them. How efficiently 2,6-dimethylnaphthalene is concentrated is a technical challenge.

In order to separate out 2,6-dimethylnaphthalene, cooling crystallization methods, adsorption methods, and the like have been suggested. However, since 2,6-dimethylnaphthalene and 2,7-dimethylnaphthalene form a eutectic mixture, cooling crystallization decreases the yield of 2,6-dimethylnaphthalene and increases the cost of purification.

On the other hand, Japanese Examined Patent Application Publication No. 49-27578 discloses a method for separating out 2,6-dimethylnaphthalene by adsorption, in which a dimethylnaphthalene isomer mixture is supplied to an adsorption column packed with Y-type zeolite, serving as an adsorbent, to be concentrated by adsorption and, further, the discharged solution is separated into 2,7-dimethylnaphthalene and 2,6-dimethylnaphthalene by cooling crystallization.

Also, Japanese Unexamined Patent Application Publication No. 6-65114 suggests that a Y-type zeolite containing potassium ions be used as an adsorbent for separating out 2,6-dimethylnaphthalene. In the embodiment of the above-described Japanese Unexamined Patent Application Publication No. 6-65114, KNa-Y type zeolite pellets in which 98% of cation sites are exchanged for potassium ions are packed in a column having an inner diameter of 1.07 cm and a length of 50 cm.

However, according to these adsorption methods, the concentration of 2,6-dimethylnaphthalene in dimethylnaphthalene isomer mixtures does not reach a sufficient level. While the adsorption methods need to be improved, suitable methods for operating adsorption columns to fully bring out the performance of adsorbents have not been found yet.

Although it is known that, for example, adsorbents having a smaller grain size improve the separation performance thereof, these adsorbents increase the pressure loss of the adsorption column. Also, an adsorption column having a higher ratio of the length to the inner diameter thereof increases the linear velocity of fluid supplied to the adsorption column, thereby reducing the diffusion resistance, at the surface of the adsorbent, of dimethylnaphthalene in the adsorption column. Thus, the separation performance is enhanced; however, the pressure loss of the column increases.

SUMMARY OF THE INVENTION

Accordingly, an object of the present invention is to provide a method for fully bringing out the performance of adsorbents and selectively concentrating 2,6-dimethylnaphthalene in a dimethylnaphthalene isomer mixture.

The inventors have conducted intensive research to accomplish this object and found a factor for fully bring out the performance of adsorbents. The factor is expressed by $(u^{1/3}/\epsilon)d^{-5/3}$ ($m^{5/3}$ $s^{-1/3}$ $kg^{-1}$), wherein u represents the linear velocity (m/s) of a solution of dimethylnaphthalene isomer mixture supplied to an adsorption column, $\epsilon$ represents the packing density ($kg/m^3$) of a Y-type zeolite adsorbent, and d represents the grain size (m) of the adsorbent.

According to an aspect of the present invention, a method for concentrating 2,6-dimethylnaphthalene in a dimethylnaphthalene isomer mixture in which o-xylene contains the 2,6-dimethylnaphthalene and 2,7-dimethylnaphthalene. The method includes the step of supplying the dimethylnaphthalene isomer mixture to an adsorption column packed with Y-type zeolite. The value of $(u^{1/3}/\epsilon)d^{-5/3}$ is set at 14 ($m^{5/3}$ $s^{-1/3}$ $kg^{-1}$) or more. u represents the linear velocity (m/s) of the solution of dimethylnaphthalene isomer mixture supplied to the adsorption column, $\epsilon$ represents the packing density ($kg/m^3$) of the Y-type zeolite, and d represents the grain size (m) of the Y-type zeolite.

The linear velocity u (m/s) is derived from the expression u=F/S, wherein S represents the cross section ($m^2$) of the adsorption column and F represents the flow rate ($m^3/s$) of the fluid supplied to the adsorption column.

The packing density $\epsilon$ ($kg/m^3$) is derived from the expression $\epsilon$=W/V, wherein W represents the weight (kg) of the Y-type zeolite and V represents the volume ($m^3$) of the adsorption column.

In order to set the above-described value of the expression $(u^{1/3}/\epsilon)d^{-5/3}$ at 14 ($m^{5/3}$ $sec^{-1/3}$ $kg^{-1}$) or more, preferably, the linear velocity u is in the range of $1\times10^{-5}$ to $1\times10^{-3}$ m/s, the packing density $\epsilon$ is in the range of 500 to 1000 $kg/m^3$, and the grain size d is in the range of $1\times10^{-4}$ to $5\times10^{-3}$ m.

Preferably, at least part of ion-exchanging sites of the Y-type zeolite are exchanged for potassium ions.

DESCRIPTION OF THE PREFERRED EMBODIMENTS

Figure 1:
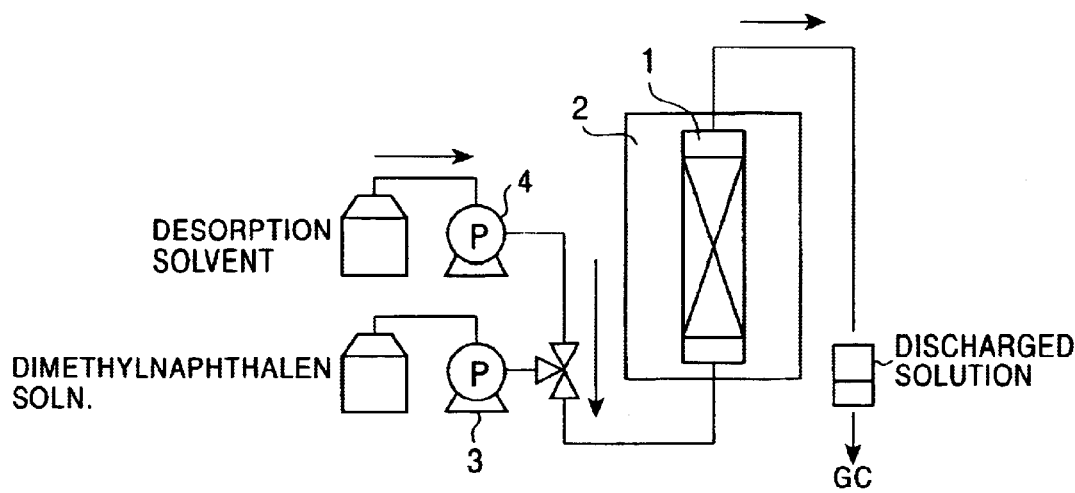
FIG. 1 is a schematic illustration of a system for concentrating 2,6-dimethylnaphthalene according to a method of the present invention.

A method of the present invention is used for concentrating 2,6-dimethylnaphthalene in a dimethylnaphthalene isomer mixture in which o-xylene contains 2,6-dimethylnaphthalene and 2,7-dimethylnaphthalene. The method is conducted by supplying the isomer mixture to an adsorption column packed with Y-type zeolite. The method is characterized in that the value derived from the expression $(u^{1/3}/\epsilon)d^{-5/3}$ is 14 ($m^{5/3}$ $s^{-1/3}$ $kg^{-1}$) or more, wherein u is the linear velocity (m/s) of the isomer mixture supplied, $\epsilon$ is the packing density (kg/m$^3$) of the Y-type zeolite, and d is the grain size (m) of the Y-type zeolite.

The recovery ratio of 2,6-dimethylnaphthalene in the discharged solution must be 90% or more with respect to the supplied 2,6-dimethylnaphthalene and, preferably, the concentration ratio of the 2,6-dimethylnaphthalene to 2,7-dimethylnaphthalene is 2.0 or more, from the view point of economical efficiency in the manufacturing process of 2,6-dimethylnaphthalene. In order to satisfy these requirements, the value of the above-described expression $(u^{1/3}/\epsilon)d^{-5/3}$ must be 14 (m$^{5/3}$ s$^{-1/3}$ kg$^{-1}$) or more.

The dimethylnaphthalene isomer mixture used in the method of the present invention may contain other hydrocarbons and it may be diluted with o-xylene. Also, an undiluted dimethylnaphthalene isomer mixture may be used.

Y-type zeolite is used as an adsorbent in the method of the present invention. Preferably, part of the ion-exchanging sites of the Y-type zeolite are exchanged for potassium ions. A small grain size of the adsorbent is desired because a smaller grain size reduces the diffusion time of the adsorbent. However, an excessively small grain size increases the pressure loss of the adsorption column. Preferably, the grain size d of the adsorbent is in the range of 1×10$^{-4}$ to 5×10$^{-3}$ m. More preferably, the grain size d is in the range of 5×10$^{-4}$ to 3×10$^{-3}$ m. The adsorbent can have any shape as long as the grain size d is within the above-described range, and it may be in the shape of a pellet, bead, or granule. If the Y-type zeolite is in the shape of a pellet, the grain size d (m) of the Y-type zeolite is defined by the equation d=$(S/\pi)^{1/2}$ on a bead basis. S is the surface area (m$^2$) of a pellet of the Y-type zeolite.

Also, the packing density $\epsilon$ of the Y-type zeolite in an adsorption column is important for concentrating 2,6-dimethylnaphthalene effectively. A higher packing density $\epsilon$ of the adsorbent increases the amount of packed adsorbent per volume and, therefore, leads to an adsorption column packed with a larger amount of adsorbent. The packing density $\epsilon$ depends on the shape (for example, powder, granule, pellet, or sphere) and the size of the Y-type zeolite, and preferably, the packing density $\epsilon$ is in the range of 500 to 1000 kg/m$^3$.

The linear velocity u of the dimethylnaphthalene isomer mixture and a desorbent supplied to the adsorption column is, preferably, in the range of 1×10$^{-5}$ to 1×10$^{-3}$ m/s. As the linear velocity u increases, the thickness of a laminar film formed between the adsorbent and the dimethylnaphthalene isomer mixture becomes smaller and, accordingly, the mass transfer becomes faster. However, an excessively high linear velocity u increases the pressure loss of the adsorption column.

The linear velocity u, the packing density $\epsilon$, and the grain size d of the adsorbent are set such that the value derived from the expression $(u^{1/3}/\epsilon)d^{-5/3}$ is 14 (m$^{5/3}$ s$^{-1/3}$ kg$^{-1}$) or more and, therefore, they must be set within the ranges described above.

Preferably, the temperature of the adsorption column is in the range of 100 to 250° C. during operation. A higher temperature decreases the amount of the desorbing solvent required to desorb the dimethylnaphthalene. However, operation at a high temperature causes the operation to be under high pressure, and this is not suitable. More preferably, the temperature of the adsorption column during operation is in the range of 100 to 200° C., and still more preferably in the range of 150 to 200° C.

The adsorbent can be recycled for the following concentration of 2,6-dimethylnaphthalene by desorbing adsorbates. Any desorbent capable of desorbing adsorbates can be used, and preferably, o-xylene is used.

Why the value of $(u^{1/3}/\epsilon)d^{-5/3}$ must be 14 (m$^{5/3}$ s$^{-1/3}$ kg$^{-1}$) or more will now be described with reference to the experimental results.

FIG. 1 shows an exemplary system used in the method of the present invention. The experiment was conducted on a laboratory scale.

An absorption column 1 in FIG. 1 is packed with Y-type zeolite. The adsorption column 1 is surrounded by a heater 2. A dimethylnaphthalene isomer mixture solution is supplied to the adsorption column 1 from the bottom with a pump 3. While the solution passes through the adsorption column 1, 2,7-dimethylnaphthalene is selectively adsorbed, and thus concentrated 2,6-dimethylnaphthalene is discharged. After the pump 3 stops supplying the dimethylnaphthalene isomer mixture solution, a desorbent is supplied to the adsorption column 1 with another pump 4. The 2,7-dimethylnaphthalene is eluted in the desorbent to be discharged from the adsorption column 1.

Four columns of 7.6 mm in inner diameter and 750 mm in length; 20 mm in inner diameter and 100 mm in length; 30 mm in inner diameter and 50 mm in length; and 40 mm in inner diameter and 1000 mm in length were used for the adsorption column at a temperature of 180° C.

Three K–Y type zeolites, in which at least part of ion-exchanging sites of the Y-type zeolite were exchanged for potassium ions, were used as the adsorbent, and they were each in the shape of a pellet (2.07×10$^{-3}$ m in grain size), granule (4.6×10$^{-4}$ m in grain size), or bead (5.0×10$^{-4}$ m in grain size).

The following eight dimethylnaphthalene isomers were used: 1,2-dimethylnaphthalene, 1,3-dimethylnaphthalene, 1,4-dimethylnaphthalene, 1,6-dimethylnaphthalene, 1,7-dimethylnaphthalene, 2,3-dimethylnaphthalene, 2,6-dimethylnaphthalene, and 2,7-dimethylnaphthalene. The isomers were each diluted with o-xylene in the proportion of 1 to 1 and then a dimethylnaphthalene isomer mixture solution was prepared such that the content of 2,6-dimethylnaphthalene and 2,7-dimethylnaphthalene was 10% (the ratio of 2,6-dimethylnaphthalene to 2,7-dimethylnaphthalene was 1.0).

Dimethylnaphthalene solutions which were discharged from the adsorption column in a sequential process of adsorption-desorption were subjected to gas chromatography and the concentrations of 2,6-dimethylnaphthalene and 2,7-dimethylnaphthalene in each discharged solution were determined. Then, the concentration ratio of 2,6-dimethylnaphthalene to 2,7-dimethylnaphthalene and the recovery ratio of 2,6-dimethylnaphthalene in the sequential process of adsorption-desorption were derived from the volume and the concentrations of the discharged dimethylnaphthalene isomers.

Figure 2:
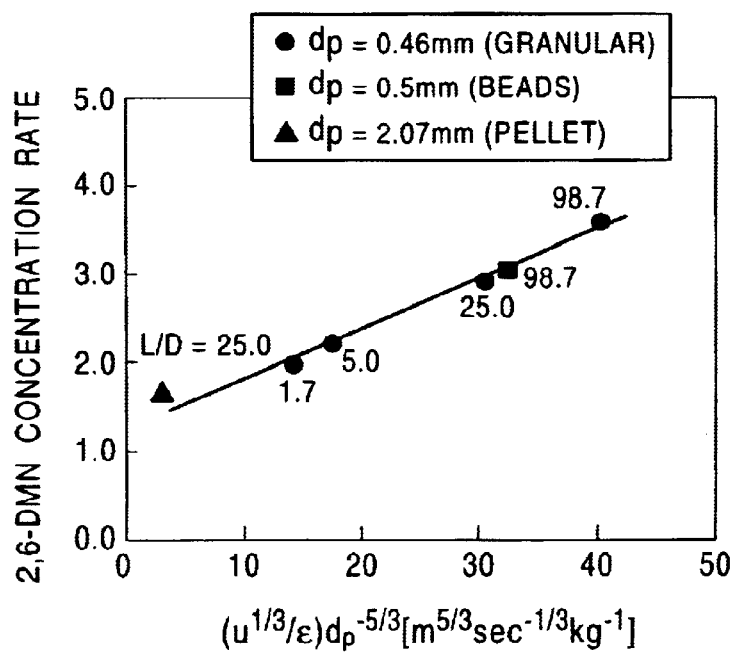
FIG. 2 is a graph showing the relationship between the concentration ratio of 2,6-dimethylnaphthalene and the value derived from the expression $(u^{1/3}/\epsilon)d^{-5/3}$ ($m^{5/3}$ $s^{-1/3}$ $kg^{-1}$).

Table 1 shows the conditions of the concentration process, the value of the expression $(u^{1/3}/\epsilon)d^{-5/3}$ (m$^{5/3}$ s$^{-1/3}$ kg$^{-1}$), and the concentration ratio of 2,6-dimethylnaphthalene to 2,7-dimethylnaphthalene after the sequential process of the adsorption-desorption when the recovery ratio of 2,6-dimethylnaphthalene was 90%. FIG. 2 shows the relationship between the concentration ratio of 2,6-dimethylnaphthalene and the value of the expression $(u^{1/3}/\epsilon)d^{-5/3}$ (m$^{5/3}$ s$^{-1/3}$ kg$^{-1}$). y-axis represents the concentration ratio of 2,6-dimethylnaphthalene and the x-axis represents the value derived from the expression $(u^{1/3}/\epsilon)d^{-5/3}$ (m$^{5/3}$ s$^{-1/3}$ kg$^{-1}$).

TABLE 1

| No. | Adsorption column size (mm) diameter (D) | Length (L) | L/D | Shape | Depth (m) | Packing density $\epsilon$ (kg/m³) | Linear velocity u (m/s) | Concentration ratio[*1] | Expression value[*2] ($m^{5/3} s^{-1/3} kg^{-1}$) |
|---|---|---|---|---|---|---|---|---|---|
| 1 | 7.6 | 750 | 98.7 | Bead | $5.0 \times 10^{-4}$ | 711 | $3.75 \times 10^{-4}$ | 3 | 32 |
| 2 | 7.6 | 750 | 98.7 | granule | $4.6 \times 10^{-4}$ | 665 | $3.75 \times 10^{-4}$ | 3.5 | 40 |
| 3 | 20 | 100 | 5.0 | granule | $4.6 \times 10^{-4}$ | 665 | $5.0 \times 10^{-5}$ | 2.2 | 18 |
| 4 | 30 | 50 | 1.7 | granule | $4.6 \times 10^{-4}$ | 665 | $2.5 \times 10^{-5}$ | 2.0 | 14 |
| 5 | 40 | 1000 | 25.0 | pellet | $2.7 \times 10^{-3}$ | 639 | $2.67 \times 10^{-5}$ | 1.7 | 3 |
| 6 | 40 | 1000 | 25.0 | granule | $4.6 \times 10^{-4}$ | 665 | $2.67 \times 10^{-5}$ | 2.9 | 31 |

[*1]Concentration ratio of 2,6-dimethylnaphthalene to 2,7-dimethylnaphthalene
[*2]$(u^{1/3}\epsilon)d^{-5/3}$ FIG. 2 shows a correlation between the concentration ratio of 2,6-dimethylnaphthalene and the value of the expression $(u^{1/3}/\epsilon)d^{-5/3}$ ($m^{5/3} s^{-1/3} kg^{-1}$). In other words, the concentration ratio of 2,6-dimethylnaphthalene, that is, the performance of the adsorbent in an adsorption process, can be estimated by the value derived from the expression $(u^{1/3}/\epsilon)d^{-5/3}$ ($m^{5/3} s^{-1/3} kg^{-1}$). Therefore, by determining the conditions for the concentration of 2,6-dimethylnaphthalene and the type of adsorbent, and by calculating the value of the expression $(u^{1/3}/\epsilon)d^{-5/3}$ ($m^{5/3} s^{-1/3} kg^{-1}$) and using the graph in FIG. 2, the performance of the adsorbent can be estimated without attempting a test operation on an actual scale.

Also, it has been shown that when the value of the expression $(u^{1/3}/\epsilon)d^{-5/3}$ is 14 ($m^{5/3} s^{-1/3} kg^{-1}$) or more, the concentration ratio of 2,6-dimethylnaphthalene to 2,7-dimethylnaphthalene is 2.0 or more.

EXAMPLE

An example of the method for concentrating 2,6-dimethylnaphthalene of the present invention, conducted on an actual plant scale will now be described.

The following eight dimethylnaphthalene isomers were used: 1,2-dimethylnaphthalene, 1,3-dimethylnaphthalene, 1,4-dimethylnaphthalene, 1,6-dimethylnaphthalene, 1,7-dimethylnaphthalene, 2,3-dimethylnaphthalene, 2,6-dimethylnaphthalene, and 2,7-dimethylnaphthalene. The isomers were each diluted with o-xylene in the proportion of 1 to 1 and then a dimethylnaphthalene isomer mixture solution was prepared such that the content of 2,6-dimethylnaphthalene and 2,7-dimethylnaphthalene was 10% (the ratio of 2,6-dimethylnaphthalene to 2,7-dimethylnaphthalene was 1.0).

A K-Y type zeolite having a bead shape ($0.5 \times 10^{-3}$ m in grain size) was used as an adsorbent and was packed in an adsorption column of 800 mm in inner diameter and 2000 mm in length. The packing density $\epsilon$ was 650 kg/m³.

The dimethylnaphthalene isomer mixture solution was supplied with a pump at a linear velocity u of $2.3 \times 10^{-5}$ m/s to the adsorption column, which had been heated at 180° C. in advance. After predetermined time lapse, the supply of the dimethylnaphthalene solution was stopped, and subsequently o-xylene serving as a desorbent was supplied at a linear velocity u of $2.3 \times 10^{-5}$ m/s to the adsorption column to conduct desorption. In this instance, the value of the expression $(u^{1/3}/\epsilon)d^{-5/3}$ was 14 ($m^{5/3} s^{-1/3} kg^{-1}$). Table 2 shows the size of the adsorption column, the linear velocity u and the packing density $\epsilon$ of the Y-type zeolite, the grain size d of the Y-type zeolite, the concentration ratio of 2,6-dimethylnaphthalene to 2,7-dimethylnaphthalene, and the value of the expression $(u^{1/3}/\epsilon)d^{-5/3}$ ($m^{5/3} s^{-1/3} kg^{-1}$) in this example.

TABLE 2

| | Adsorption column size (mm) diameter (D) | Length (L) | L/D | Shape | Depth (m) | Packing density $\epsilon$ (kg/m³) | Linear velocity u (m/s) | Concentration ratio[*1] | Expression value[*2] ($m^{5/3} s^{-1/3} kg^{-1}$) |
|---|---|---|---|---|---|---|---|---|---|
| Example | 800 | 2000 | 2.5 | Bead | $5.0 \times 10^{-4}$ | 650 | $2.3 \times 10^{-5}$ | 2.1 | 14 |

[*1]Concentration ratio of 2,6-dimethylnaphthalene to 2,7-dimethylnaphthalene
[*2]$(u^{1/3}\epsilon)d^{-5/3}$ The solution discharged from the adsorption column was subjected to gas chromatography. As a result, the concentration ratio of 2,6-dimethylnaphthalene to 2,7-dimethylnaphthalene was 2.1 when the recovery ratio of 2,6-dimethylnaphthalene was 90%. This concentration ratio value is subsequently equivalent to the value derived from the correlation diagram shown in FIG. 2, which was obtained by the experiment described above.

According to the present invention, when 2,6-dimethylnaphthalene is separated out from a dimethylnaphthalene isomer mixture, the concentration ratio of 2,6-dimethylnaphthalene to 2,7-dimethylnaphthalene can be set at 2.0 or more by setting the value of the expression $(u^{1/3}/\epsilon)d^{-5/3}$, which is a factor for operating an adsorption column, at 14 ($m^{5/3} s^{-1/3} kg^{-1}$) or more. In the expression, u represents the linear velocity (m/s) of a dimethylnaphthalene isomer mixture supplied to an adsorption column, $\epsilon$ represents the packing density (kg/m³) of Y-type zeolite, and d represents the grain size (m) of the Y-type zeolite.

What is claimed is:

1. A method for concentrating 2,6-dimethylnaphthalene in a dimethylnaphthalene isomer mixture in which o-xylene contains the 2,6-dimethylnaphthalene and 2,7-dimethylnaphthalene, comprising:

the step of supplying the dimethylnaphthalene isomer mixture to an adsorption column packed with Y-type zeolite, wherein the value of $(u^{1/3}/\epsilon)d^{-5/3}$ is 14 $(m^{5/3}\ s^{-1/3}\ kg^{-1})$ or more, where u represents linear velocity (m/s) of the dimethylnaphthalene isomer mixture supplied to the adsorption column, $\epsilon$ represents packing density (kg/m³) of the Y-type zeolite, and d represents grain size (m) of the Y-type zeolite.

2. A method for concentrating 2,6-dimethylnaphthalene according to claim 1, wherein the linear velocity u is in the range of $1\times10^{-5}$ to $1\times10^{-3}$ m/s.

3. A method for concentrating 2,6-dimethylnaphthalene, according to claim 1, wherein the packing density $\epsilon$ is in the range of 500 to 1000 kg/m³.

4. A method for concentrating 2,6-dimethylnaphthalene, according to claim 1, wherein the grain size d is in the range of $1\times10^{-4}$ to $5\times10^{-3}$ m.

5. A method for concentrating 2,6-dimethylnaphthalene, according to claim 1, wherein at least part of ion-exchanging sites of the Y-type zeolite are exchanged for potassium ions.

* * * * *

UNITED STATES PATENT AND TRADEMARK OFFICE
CERTIFICATE OF CORRECTION

PATENT NO.    : 6,706,939 B2  
DATED         : March 16, 2004  
INVENTOR(S)   : Nakao et al.

It is certified that error appears in the above-identified patent and that said Letters Patent is hereby corrected as shown below:

Title page,  
Item [73], Assignee, should read:  
-- [73]   Assignee:    Kabushiki Kaisha Kobe Seiko Sho (Kobe Steel, Ltd.), Kobe (JP) --

Signed and Sealed this

Twenty-second Day of February, 2005

JON W. DUDAS  
*Director of the United States Patent and Trademark Office*